(12) United States Patent
Nemoto et al.

(10) Patent No.: US 7,828,776 B2
(45) Date of Patent: Nov. 9, 2010

(54) CHEMICAL LIQUID INJECTION SYSTEM

(75) Inventors: Shigeru Nemoto, Tokyo (JP); Nobuhisa Tano, Tokyo (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 251 days.

(21) Appl. No.: 11/911,139

(22) PCT Filed: Apr. 10, 2006

(86) PCT No.: PCT/JP2006/307586

§ 371 (c)(1),
(2), (4) Date: Oct. 10, 2007

(87) PCT Pub. No.: WO2006/109778

PCT Pub. Date: Oct. 19, 2006

(65) Prior Publication Data

US 2009/0018494 A1 Jan. 15, 2009

(30) Foreign Application Priority Data

Apr. 11, 2005 (JP) ............................ 2005-113065

(51) Int. Cl.
*A61M 3/00* (2006.01)
*A61M 1/00* (2006.01)
*A61M 31/00* (2006.01)
(52) U.S. Cl. ..................... 604/189; 604/151; 604/65
(58) Field of Classification Search ............ 604/65–69, 604/151–153, 189
See application file for complete search history.

(56) References Cited

U.S. PATENT DOCUMENTS

| 5,840,026 A | 11/1998 | Uber, III et al. | |
| 2001/0056258 A1* | 12/2001 | Evans | 604/131 |
| 2005/0029277 A1* | 2/2005 | Tachibana | 221/9 |
| 2005/0110640 A1* | 5/2005 | Chung | 340/572.1 |
| 2005/0150944 A1* | 7/2005 | Melick et al. | 235/375 |
| 2005/0177129 A1* | 8/2005 | Pacha et al. | 604/500 |

(Continued)

FOREIGN PATENT DOCUMENTS

EP 1 433 456 A1 6/2004

(Continued)

OTHER PUBLICATIONS

Chinese Office Action issued on Dec. 25, 2009 by the Chinese Patent Office for the counterpart Chinese Patent Application No. 200680018429.7.

*Primary Examiner*—Nicholas D Lucchesi
*Assistant Examiner*—Rebecca E Eisenberg
(74) *Attorney, Agent, or Firm*—Knobbe, Martens Olson & Bear LLP

(57) ABSTRACT

The present invention provides a chemical liquid injection system in which a chemical liquid injector can detect whether or not the injection of a liquid from a liquid syringe into a patient is inappropriate for a personal reason such as the development of a side effect although the liquid is of an appropriate type for the injection system, and the chemical liquid injector can issue an alarm to notify the inappropriate injection. Chemical liquid injector 100 acquires a product ID of the liquid recorded on liquid chip 214 of liquid syringe 200 and an inappropriate ID recorded in a electric chart to output a notification when the product ID matches the inappropriate ID.

17 Claims, 8 Drawing Sheets

U.S. PATENT DOCUMENTS

2008/0045901 A1 * 2/2008 Nemoto et al. .............. 604/131

FOREIGN PATENT DOCUMENTS

| JP | 8-315051 | 11/1996 |
| JP | 2002-165882 A | 6/2002 |
| JP | 2002-334153 | 11/2002 |
| JP | 2004-298550 A | 10/2004 |
| WO | WO 03/024385 A1 | 3/2003 |
| WO | 2004/088567 A2 | 10/2004 |
| WO | WO 2006006643 A1 * | 1/2006 |

* cited by examiner

CHEMICAL LIQUID INJECTION SYSTEM

This application is the U.S. National Phase under 35 U.S.C. §371 of International Application PCT/JP2006/307586, filed Apr. 10, 2006, which claims priority to Japanese Patent Application No. 2005-113065, filed Apr. 11, 2005. The International Application was published under PCT Article 21(2) in a language other than English.

TECHNICAL FIELD

The present invention relates to a chemical liquid injection system for injecting a liquid into a patient from a liquid syringe with a chemical liquid injector, and more particularly, to a chemical liquid injection system for injecting a contrast medium into a patient whose diagnostic images are taken by an imaging diagnostic apparatus such as a CT (Computed Tomography) scanner.

BACKGROUND ART

Presently available imaging diagnostic apparatuses for capturing diagnostic images of patients include CT scanners, MRI (Magnetic Resonance Imaging) apparatuses, PET (Positron Emission Tomography) apparatuses, ultrasonic diagnostic apparatuses, CT angiography apparatuses, MRA (MR angiography) apparatuses and the like. When the above-mentioned imaging diagnostic apparatuses are used, a liquid such as a contrast medium and physiological saline may be injected into a patient. Chemical liquid injectors for automatically performing the injection have been put into practical use.

Such a chemical liquid injector has a liquid injection mechanism formed of a driving motor, a slider mechanism and the like, for example. A liquid syringe is removably mounted on the injector. The liquid syringe typically comprises a cylinder member and a piston member slidably inserted in the cylinder member. There are a pre-filled type and a refill type in the liquid syringe.

The liquid syringe of the pre-filled type includes a cylinder member filled with a liquid and is wholly sealed by a packing material for shipment. The liquid syringe of the refill type includes a cylinder member which can be filled with a desired liquid by a user. For simplicity, the following description will be made assuming that the liquid syringe of the pre-filled type is used.

For injecting the liquid into a patient from the liquid syringe of the abovementioned type, an operator prepares for a liquid syringe containing an appropriate liquid and takes out the liquid syringe from the packing material. The operator connects the liquid syringe to a patient through an extension tube and mounts the liquid syringe on a liquid injection mechanism of a chemical liquid injector. In response to a predetermined operation, the chemical liquid injector moves the piston member relative to the cylinder member with the liquid injection mechanism to inject the liquid into the patient from the liquid syringe.

The operator determines the rate at which the liquid is injected and the total quantity of the liquid to be injected in view of the type of the liquid and the like, and enters data representing the rate and total quantity into the chemical liquid injector. The chemical liquid injector injects the liquid into the patient based on the entered data. For example, when a contrast medium is injected as the liquid, the image contrast of the patient is changed to allow the imaging diagnostic apparatus to capture a favorable diagnostic image of the patient.

Some chemical liquid injectors can inject physiological saline as well as the contrast medium into the patient. In such a chemical liquid injector, the operator enters as desired an instruction to inject the physiological saline following the completion of the injection of the contrast medium, together with data representing the injection rate and total quantity of the physiological saline, into the chemical liquid injector. The chemical liquid injector first injects the contrast medium into the patient based on the entered data and then automatically injects the physiological saline. The subsequently injected physiological saline can push the previously injected contrast medium to reduce the consumption of the contrast medium and also can reduce artifacts in the captured image.

Some chemical liquid injection system currently proposed have a data storing means such as an RFID chip and a bar code put on a liquid syringe such that the data stored thereon is read out by a chemical liquid injector (see, for example, Patent Documents 1 and 2 below).

Patent Document 1: U.S. Pat. No. 5,840,026
Patent Document 2: Japanese Patent Laid-Open No. 2004-298550

DISCLOSURE OF THE INVENTION

Subject to be Solved by the Invention

In the chemical liquid injection system as described above, the chemical liquid injector can detect the type and the like of the liquid in the liquid syringe of the pre-filled type, so that it is possible to prevent the medical malpractice of injection of a wrong liquid into a patient, for example. However, a patient may experience a side effect even when a correct liquid is injected into the patient.

For example, a contrast medium for CT is typically made mainly of iodine, and the structural formula of iodine slightly varies among products. Injection of an appropriate contrast medium for CT into a patient of a CT scanner may or may not cause a side effect depending on a specific combination of a product of the contrast medium and the patient.

In the chemical liquid injection system as described above in which the chemical liquid injector reads various types of data from the data storing means on the liquid syringe, the chemical liquid injector can detect whether the liquid in the liquid syringe is a contrast medium for CT or not. However, the development of a side effect from the liquid varies from patient to patient and cannot be detected by the chemical liquid injector.

The present invention has been made in view of the above-mentioned problem, and it is an object thereof to provide a chemical liquid injection system in which a chemical liquid injector can detect whether or not the injection of a liquid from a liquid syringe into a patient is inappropriate for a personal reason such as the development of a side effect although the liquid is of an appropriate type for the injection system, and the chemical liquid injector can issue an alarm to notify the inappropriate injection.

Means to Solve the Subject

The chemical liquid injection system according to the present invention comprises a liquid syringe and a chemical liquid injector. The liquid syringe includes a cylinder member filled with a liquid and a piston member slidably inserted into the cylinder member interchangeably. The chemical liquid injector injects the liquid into a patient by relatively moving the cylinder member and the piston member of the liquid syringe with a liquid injection mechanism.

In a chemical liquid injection system according to a first aspect, the liquid syringe has a data storing means, and the chemical liquid injector includes a liquid data acquiring means, a patient chart data acquiring means, a data comparing means, and an alarm notifying means. The data storing means of the liquid syringe records at least data of a product ID of the filled liquid. The liquid data acquiring means of the chemical liquid injector acquires the product ID from the data storing means. The patient chart data acquiring means acquires an inappropriate ID from an external electronic chart, at least a product ID of the liquid inappropriate for injection being registered as the inappropriate ID in the electronic chart for each of the patients. The data comparing means compares the acquired product ID and the inappropriate ID. The alarm notifying means notifies an alarm when the product ID matches the inappropriate ID. Thus, for example when the liquid to be injected into the patient is of the appropriate type but is inappropriate for injection, that fact is detected by the chemical liquid injector and an alarm is issued.

In a chemical liquid injection system according to a second aspect of the present invention, a data storing means of a liquid syringe records at least data of a contained ingredient of a filled liquid, and a liquid data acquiring means of a chemical liquid injector acquires the contained ingredient from the data storing means. A patient chart data acquiring means acquires an inappropriate ingredient from an external electronic chart, at least a contained ingredient inappropriate for injection being registered as the inappropriate ingredient in the electronic chart for each of patients. A data comparing means compares the acquired contained ingredient and the inappropriate ingredient. An alarm notifying means notifies an alarm when the contained ingredient matches the inappropriate ingredient. Thus, for example when the liquid to be injected into the patient is of the appropriate type but is inappropriate for injection, that fact is detected by the chemical liquid injector and an alarm is issued.

In a chemical liquid injection system according to a third aspect of the present invention, a chemical liquid injector includes a liquid data acquiring means, a data retrieving means, a patient chart data acquiring means, a data comparing means, and an alarm notifying means. The liquid data acquiring means of the chemical liquid injector acquires the product ID from the data storing means of a liquid syringe. The data retrieving means retrieves a contained ingredient from an external liquid database with the acquired product ID, at least the contained ingredient being registered in the liquid database for each of the product IDs. The patient chart data acquiring means acquires an inappropriate ingredient from an external electronic chart, at least a contained ingredient of the liquid inappropriate for injection being registered as the inappropriate ingredient in the electronic chart for each of the patients. The data comparing means compares the retrieved contained ingredient and the acquired inappropriate ingredient. The alarm notifying means notifies an alarm when the contained ingredient matches the inappropriate ingredient. Thus, for example when the liquid to be injected into the patient is of the appropriate type but is inappropriate for injection, that fact is detected by the chemical liquid injector and an alarm is issued.

In a chemical liquid injection system according to a fourth aspect of the present invention, a chemical liquid injector includes a liquid data acquiring means, an ingredient storing means, a data retrieving means, a patient chart data acquiring means, a data comparing means, and an alarm notifying means. The liquid data acquiring means of the chemical liquid injector acquires the product ID from the data storing means. The ingredient storing means registers data of a contained ingredient for each of the product IDs. The data retrieving means retrieves the contained ingredient from the ingredient storing means with the acquired product ID. The patient chart data acquiring means acquires an inappropriate ingredient from an external electronic chart, at least a contained ingredient of the liquid inappropriate for injection being registered as the inappropriate ingredient in the electronic chart for each of the patients. The data comparing means compares the retrieved contained ingredient and the acquired inappropriate ingredient. The alarm notifying means notifies an alarm when the contained ingredient matches the inappropriate ingredient. Thus, for example when the liquid to be injected into the patient is of the appropriate type but is inappropriate for injection, that fact is detected by the chemical liquid injector and an alarm is issued.

In a chemical liquid injection system according to a fifth aspect of the present invention, a data storing means of a liquid syringe records at least data of a chemical classification of a filled liquid, and a liquid data acquiring means of a chemical liquid injector acquires the chemical classification from the data storing means. A patient chart data acquiring means acquires an inappropriate classification from an external electronic chart, at least a chemical classification inappropriate for injection being registered as the inappropriate classification in the electronic chart for each of the patients. A data comparing means compares the acquired chemical classification and the inappropriate classification. An alarm notifying means notifies an alarm when the chemical classification matches the inappropriate classification. Thus, for example when the liquid to be injected into the patient is of the appropriate type but is inappropriate for injection, that fact is detected by the chemical liquid injector and an alarm is issued.

In a chemical liquid injection system according to a sixth aspect of the present invention, a liquid data acquiring means of a chemical liquid injector acquires a product ID from a data storing means of a liquid syringe. A patient chart data acquiring means acquires an inappropriate classification from an external electronic chart, at least a chemical classification of the liquid inappropriate for injection being registered as the inappropriate classification in the electronic chart for each of the patients. A data retrieving means retrieves a chemical classification from an external liquid database with the acquired product ID, at least the chemical classification being registered in the liquid database for each of the product IDs. A data comparing means compares the retrieved chemical classification and the acquired inappropriate classification. An alarm notifying means notifies an alarm when the chemical classification matches the inappropriate classification. Thus, for example when the liquid to be injected into the patient is of the appropriate type but is inappropriate for injection, that fact is detected by the chemical liquid injector and an alarm is issued.

In a chemical liquid injection system according to a seventh aspect of the present invention, a liquid data acquiring means of a chemical liquid injector acquires a product ID from a data storing means of a liquid syringe. A classification storing means stores a chemical classification for each of the product IDs. A data retrieving means retrieves the chemical classification from the classification storing means with the acquired product ID. A patient chart data acquiring means acquires an inappropriate classification from an external electronic chart, at least a chemical classification of the liquid inappropriate for injection being registered as the inappropriate classification in the electronic chart for each of the patients. A data comparing means compares the retrieved chemical classification and the acquired inappropriate classification. An alarm notifying means notifies an alarm when the chemical classification matches the inappropriate classification. Thus, for example when the liquid to be injected into the patient is of the appropriate type but is inappropriate for injection, that fact is detected by the chemical liquid injector and an alarm is issued.

Various means referred to in the present invention may be arranged to perform their functions, and may comprise dedicated hardware for performing a predetermined function, a data processing apparatus whose predetermined function is given by a computer program, a predetermined function performed in a data processing apparatus according to a computer program, or a combination thereof.

Various components referred to in the present invention do not need to be a separate entity. A plurality of components may be constructed as one member, a certain component may be part of another component, or a certain component may have a portion overlapping a portion of another component.

Effect of the Invention

According to the chemical liquid injection system of the present invention, for example when the liquid to be injected into the patient is of the appropriate type but is inappropriate for injection, that fact can be detected by the chemical liquid injector and an alarm can be issued. As a result, when a patient may or may not experience a side effect depending on the product, contained ingredient, or chemical classification of a liquid, injection of any liquid causing a side effect into the patient can be prevented.

DESCRIPTION OF REFERENCE NUMERALS

Figure 1:
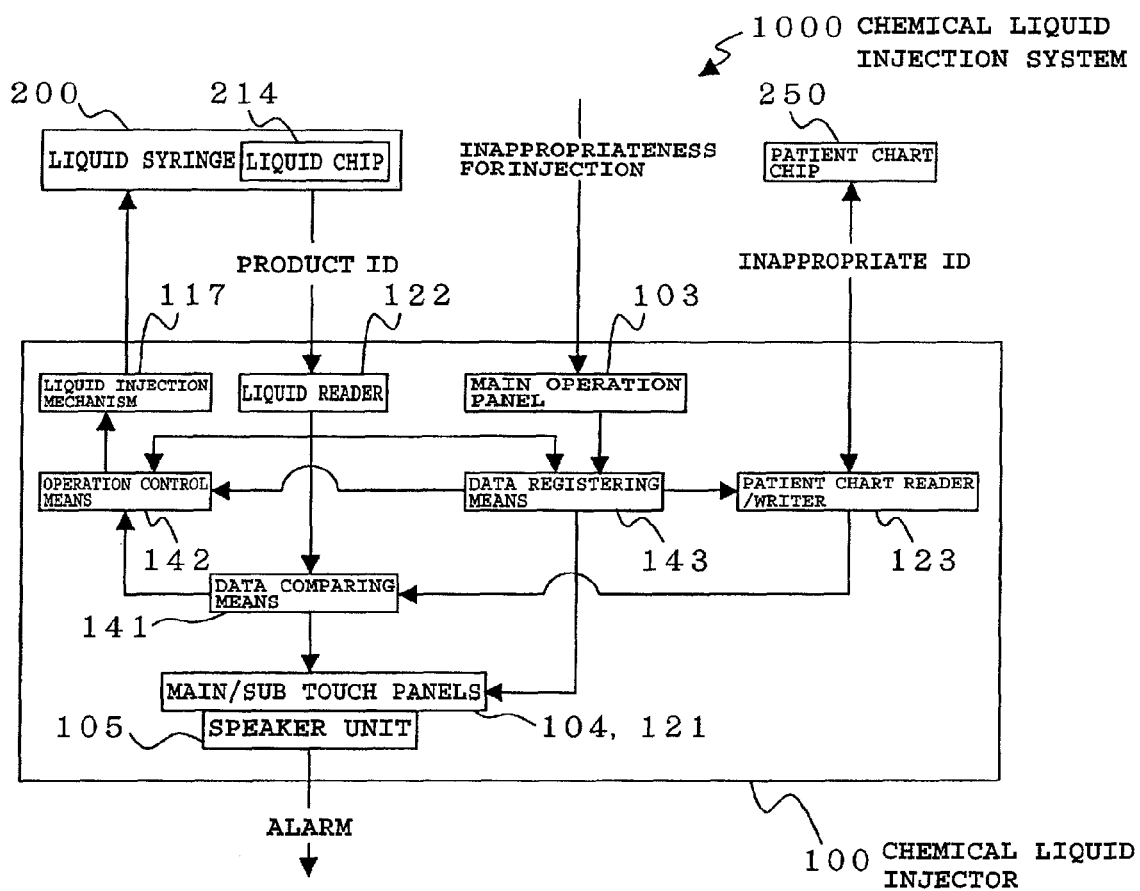
FIG. 1 is a schematic block diagram showing the logical structure of a chemical liquid injection system according to an embodiment of the present invention.

100 CHEMICAL LIQUID INJECTOR
101 INJECTION CONTROL UNIT
103 MAIN OPERATION PANEL serving as input operation means
110 Injection Execution Head
117 LIQUID INJECTION MECHANISM
121 SUB TOUCH PANEL serving as alarm notifying means
122 LIQUID READER serving as liquid data acquiring means
123 PATIENT CHART READER/WRITER serving as patient chart data acquiring means
142 Operation Control Means
141 DATA COMPARING MEANS
143 DATA REGISTERING MEANS
200 LIQUID SYRINGE
210 CYLINDER MEMBER
214 LIQUID CHIP serving as data storing means
220 PISTON MEMBER
300 CT SCANNER serving as imaging diagnostic apparatus
1000 CHEMICAL LIQUID INJECTION SYSTEM

BEST MODE FOR CARRYING THE INVENTION

Configuration of Embodiment

An embodiment of the present invention will hereinafter be described with reference to the drawings. As shown in FIGS. 1 to 4, chemical liquid injection system 1000 of the embodiment comprises chemical liquid injector 100, liquid syringe 200, and CT scanner 300 serving as an imaging diagnostic apparatus. The system is provided for injecting a liquid such as a contrast medium into a patient (not shown), described later in detail.

Figure 4:
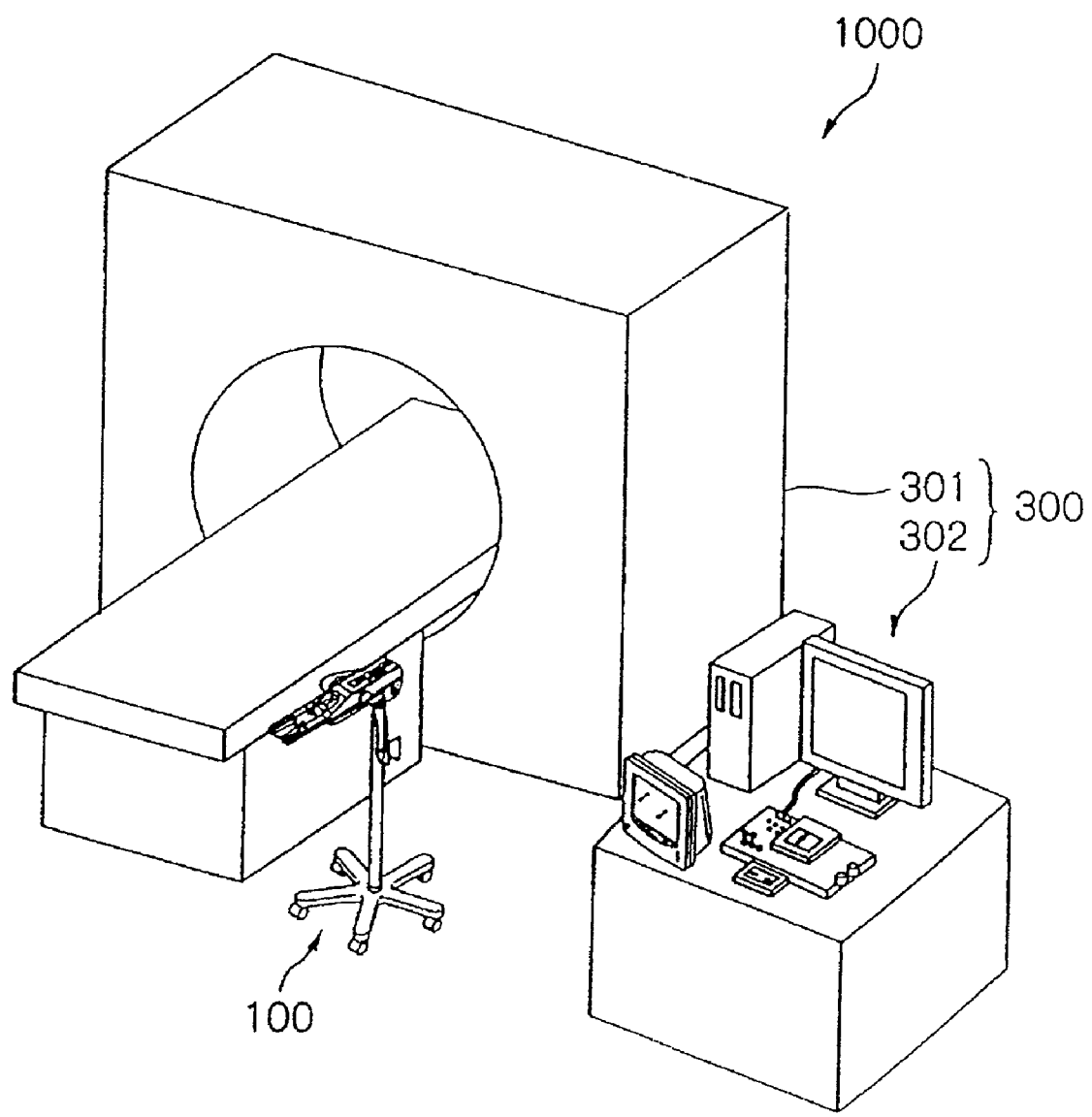
FIG. 4 is a perspective view showing the outer appearance of a CT scanner serving as an imaging diagnostic apparatus.

As shown in FIG. 4, CT scanner 300 comprises imaging diagnostic unit 301 serving as an imaging mechanism and imaging control unit 302 such that imaging diagnostic unit 301 and imaging control unit 302 are wire-connected through communication network 303. Imaging diagnostic unit 301 shoots a diagnostic image of a patient. Imaging control unit 302 controls the operation of imaging diagnostic unit 301.

Figure 2:
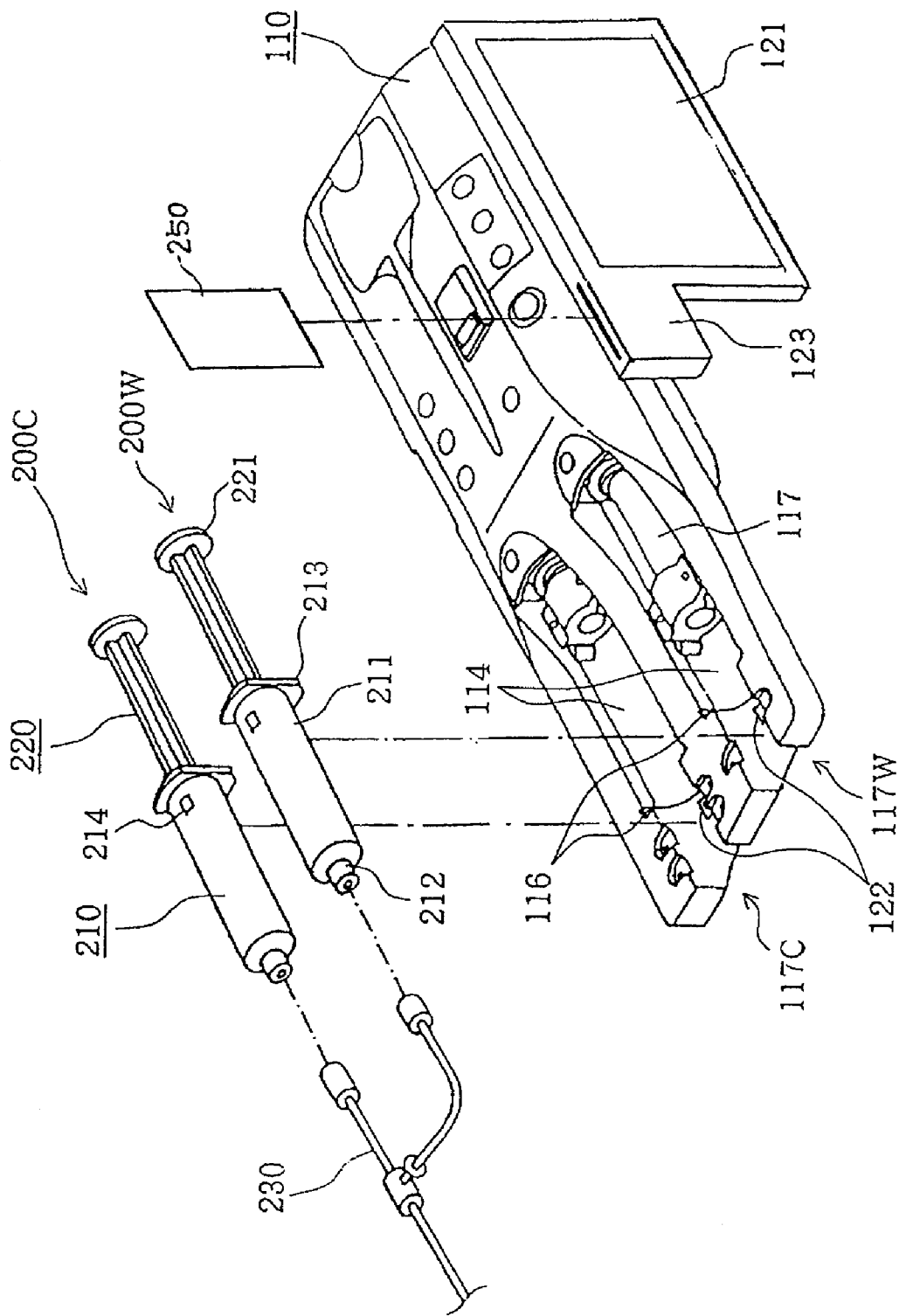
FIG. 2 is a perspective view showing a liquid syringe and a patient chart chip put on an injection execution head of a chemical liquid injector.

As shown in FIG. 2, liquid syringe 200 comprises cylinder member 210 and piston member 220 wherein piston member 220 is slidably inserted into cylinder member 210. Cylinder member 210 includes cylindrical hollow body 211 which has conduit 212 formed at the closed leading end.

The trailing end surface of body 211 of cylinder member 210 is opened and piston member 220 is inserted from the opening into the interior of body 211. Cylinder member 210 has cylinder flange 213 formed on the outer circumference of the trailing end. Piston member 220 has piston flange 221 formed on the outer circumference of the trailing end.

In chemical liquid injection system 1000 of the embodiment, liquid syringes 200 to be used are typically of the pre-filled type. Liquid syringe 200 of the pre-filled type is shipped with cylinder member 210 filled with a liquid. Liquid chip 214 formed of an RFID chip is placed as a data storing means on cylinder member 210. Liquid chip 214 has liquid data registered thereon.

The liquid data includes various types of data about liquid syringe 200 such as the capacity, the resistance to pressure of cylinder member 210, the inner diameter of cylinder member 210, and the stroke of piston member 220, and the identification data for each item, and various types of data about the contained liquid such as the product ID, the chemical classification, the contained ingredients, the viscosity, and the expiration date.

The product ID of the liquid is registered as data in association with the chemical classification, the contained ingredients, and the chemical structure of the liquid, and is not associated with the syringe capacity or the like. For example, when A company and B company produce respective products of a contrast medium for CT for heart imaging, the products have different IDs if they have different chemical classifications such as water soluble or oil-based, ionic or nonionic, and monomer or dimmer, although they are of the same liquid type, "contrast medium for CT for heart imaging."

Even when they are of the same liquid type and the same chemical classification, they have different IDs if they contain different ingredients. Even when they are of the same liquid type, the same chemical classification, and the same contained ingredients, they have different IDs if they are different in only one chemical structure of the contained ingredients.

On the other hand, when two liquid syringes 200 of the pre-filled type having a capacity of 200 ml and a capacity of 500 ml, respectively, are filled with the same liquid, those liquid syringes 200 are different products due to the different capacities but have the same product IDs of the liquid.

Liquid syringes 200 include contrast medium syringe 200C filled with a contrast medium as a liquid and physiological saline syringe 200W filled with a physiological saline as a liquid. Contrast medium/physiological saline syringes 200C and 200W are mounted on chemical liquid injector 100 simultaneously. Contrast medium/physiological saline syringes 200C and 200W mounted on chemical liquid injector 100 are connected to a patient, for example, through a syringe peripheral apparatus such as bifurcated extension tube 230.

Figure 3:
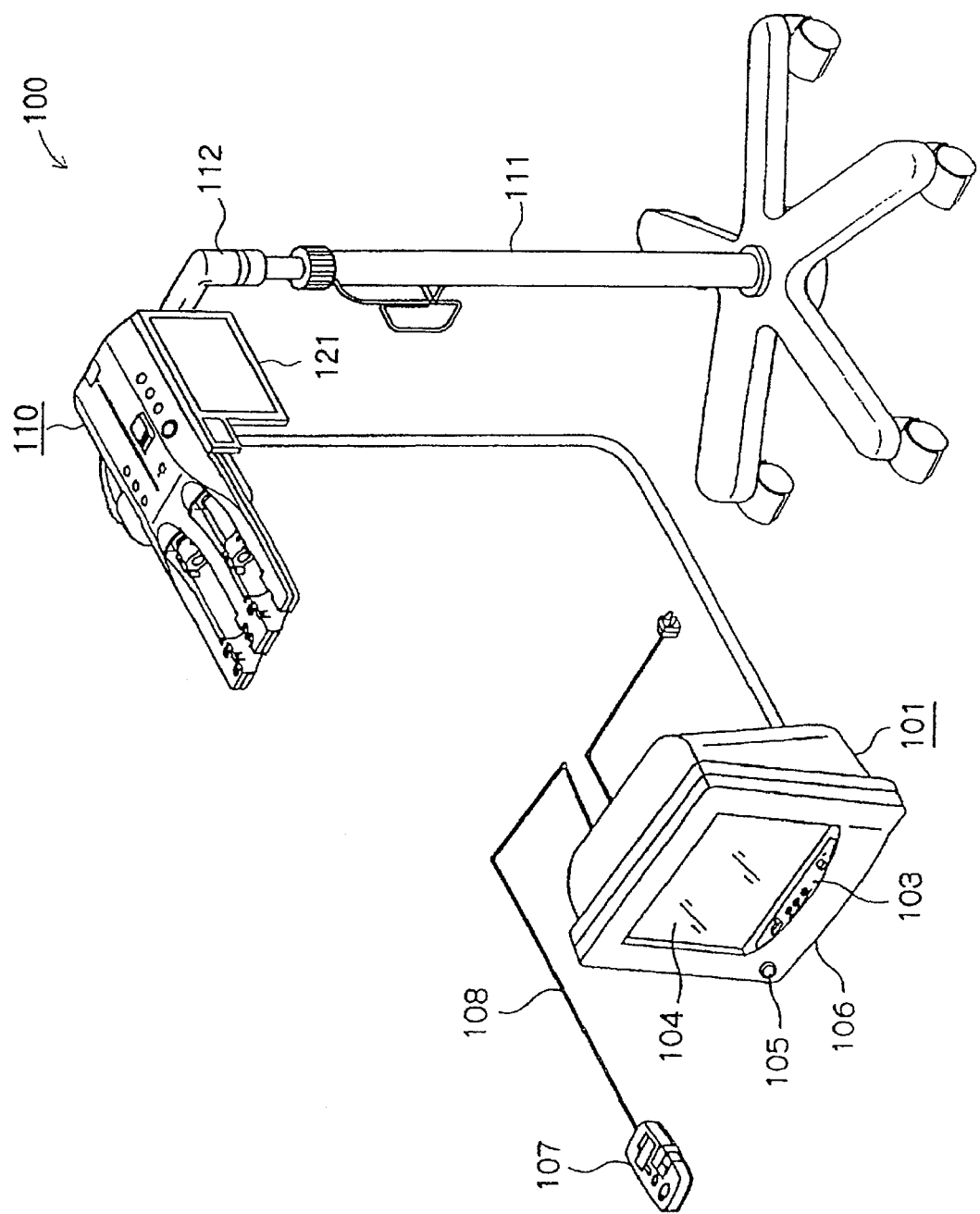
FIG. 3 is a perspective view showing the outer appearance of the chemical liquid injector.
Figure 5:
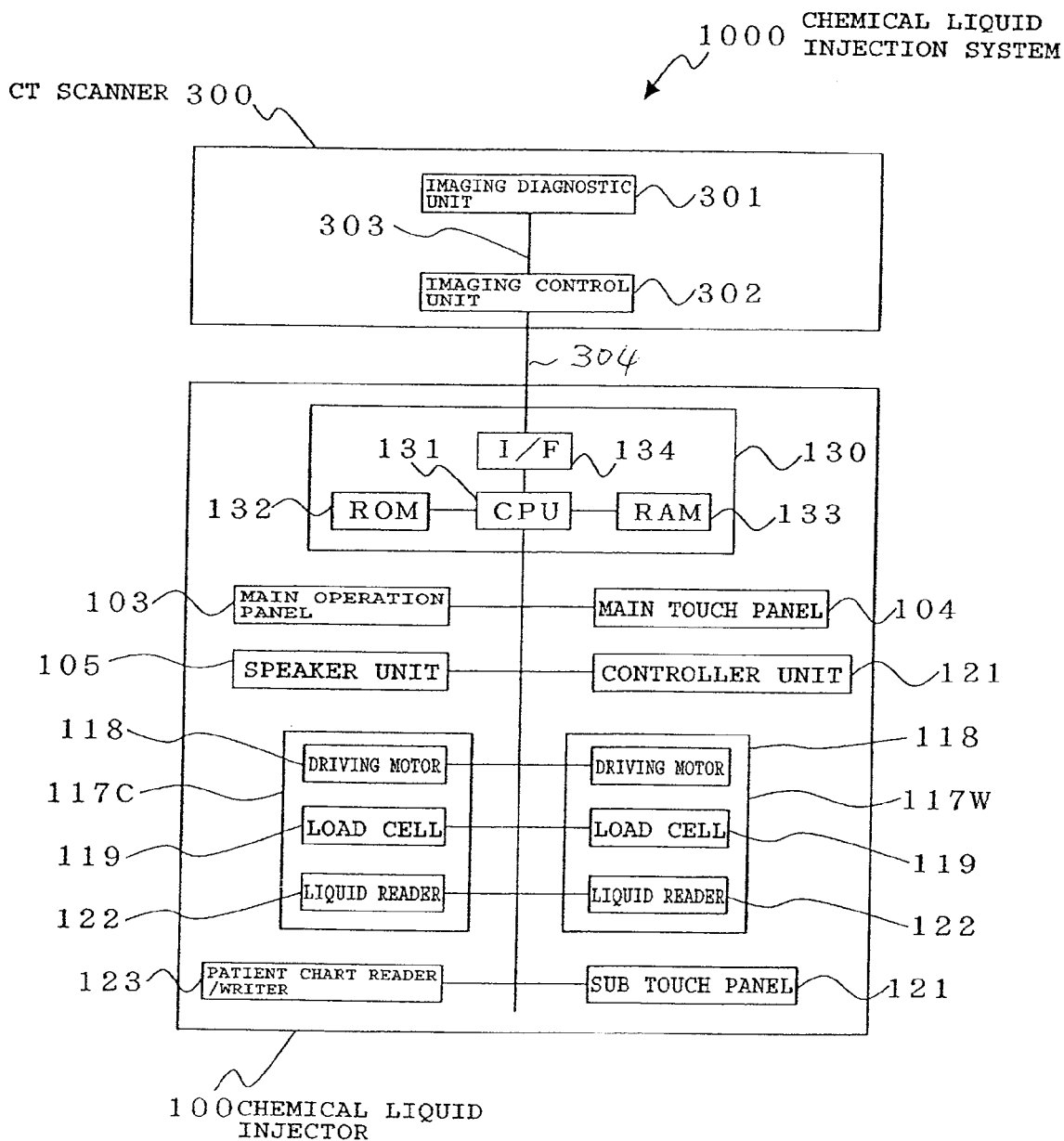
FIG. 5 is a block diagram showing the physical structure of the chemical liquid injection system.

As shown in FIG. 3, chemical liquid injector 100 of the embodiment has injection control unit 101 and injection execution head 110 constructed as separate components which are wire-connected to each other through communication cable 102. Injection execution head 110 drives liquid syringe 200 mounted thereon to inject a liquid therefrom into a patient. Injection control unit 101 controls the operation of injection execution head 110. Thus, as shown in FIG. 5, injection control unit 101 contains computer unit 130 and is connected to imaging control unit 302 of CT scanner 300 through communication network 304.

Injection control unit 101 has main operation panel 103 serving as an input operation means, main touch panel 104, and speaker unit 105, all of which are disposed on the front face of unit housing 106. Injection control unit 001 is wire-connected to controller unit 107 as a separate component through connector 108.

Injection execution head 110 is attached to the top end of caster stand 111 by movable arm 112. As shown in FIG. 2, head body 113 of injection execution head 110 has concave portion 114 formed in the upper surface as a semi-cylindrical groove for removably mounting liquid syringe 200. Cylinder holding mechanism 116 is formed in the forward section of concave portion 114 for removably holding cylinder flange 211 of liquid syringe 200. Liquid injection mechanism 117 is placed in the rearward section of concave portion 114 for holding and sliding piston flange 221.

Cylinder holding mechanism 116 is formed in concave portion 114 as a deformed reentrant groove, with which cylinder flange 211 removably engages. Each liquid injection mechanism 117 has driving motor 118 such as an ultrasonic motor and a DC motor as a driving source and slides piston member 220 through a screw mechanism (not shown) or the like. Load cell 119 is also contained in liquid injection mechanism 117 and detects the pressure applied to piston member 220.

Since contrast medium/physiological saline syringes 200C and 200W are individually put in two concave portions 114 of injection execution head 110, two concave portions 114 and two liquid injection mechanisms 117 constitute contrast medium injection mechanism 117C for injecting the contrast medium and physiological saline injection mechanism 117W for injecting the physiological saline into the patient.

Cylinder flange 213 of liquid syringe 200 is not in a simple ring shape but formed as an oval shape having two parallel sides on its outer edge. Cylinder holding mechanism 116 holds cylinder flange 213 of liquid syringe 200 in a predetermined direction to prevent rotation, so that each liquid syringe 200 has a pair of liquid chips 214 placed thereon at the upper and lower positions when it is held as described above.

Liquid reader 122 comprising an RFID reader is placed as a liquid data acquiring means at a predetermined position of concave portion 114 of injection execution head 110. Liquid reader 122 acquires the liquid data from liquid chip 214 of liquid syringe 200 which is put in concave portion 114 and held by cylinder holding mechanism 116.

Sub touch panel 121 serving as an alarm notifying means and patient chart reader/writer 123 formed of an RFID reader/writer are set on the side of the rearward section of injection execution head 110. Patient chart reader/writer 123 serves as a patient chart data acquiring means to read the data of an electronic chart from patient chart chip 250 provided for each patient.

Patient chart chip 250 is formed, for example as an IC (Integrated Circuit) card containing an RFID chip, and has the electronic chart of a patient registered as data which can be updated. The electronic chart includes the patient ID for each patient, personal data such as the gender and age, and various types of data about diseases, as well as the product ID of a liquid inappropriate for injection into the patient as an inappropriate ID.

As shown in FIG. 5, in chemical liquid injector 100 of the embodiment, the abovementioned various devices are connected to computer unit 130 which integrates and controls those various devices. Computer unit 130 comprises a so-called one-chip microcomputer provided with hardware such as CPU (Central Processing Unit) 131, ROM (Read Only Memory) 132, RAM (Random Access Memory) 133, I/F (Interface) 134 and the like.

Computer unit 130 has an appropriate computer program installed as firmware or the like in an information storage medium such as ROM 132, and CPU 131 executes various types of processing in accordance with the computer program. Computer unit 130 operates in accordance with the computer program installed as described above to allow chemical liquid injector 100 of the embodiment to logically have various means such as data comparing means 141, operation control means 142, and data registering means 143 as shown in FIG. 1.

Data comparing means 141 corresponds to the function of CPU 131 which compares the data detected by liquid reader 122 with the data detected by patient chart reader/writer 123 in accordance with the computer program installed in ROM 132 or the like and compares the product ID with the inappropriate ID. Operation control means 142 corresponds to the function of CPU 131 which controls the operation of liquid injection mechanism 117 in accordance with the computer program and controls liquid injection mechanism 117 to be inoperative when the comparison shows that the product ID matches the inappropriate ID.

More specifically, in chemical liquid injection system 1000 of the embodiment, when liquid syringe 200 is appropriately mounted on injection execution head 110 of chemical liquid injector 100, liquid reader 122 acquires the product ID from liquid chip 214 on liquid syringe 200. When patient chart chip 250 is appropriately loaded on injection execution head 110, patient chart reader/writer 123 acquires the inappropriate ID from patient chart chip 250.

After the product ID and the inappropriate ID are acquired in this manner, computer unit 130 compares them. If the product ID matches the inappropriate ID, computer unit 130 controls liquid injection mechanism 117 to be inoperative. In this case, computer unit 130 causes sub touch panel 104 or the like to serve as an alarm notifying means and output an alarm message such as "This liquid should not be injected into this patient" with display on main/sub touch panels 104 and 121 and with sound from speaker unit 105.

If liquid chip 214 of liquid syringe 200 has control data set thereon for liquid injection mechanism 117, operation control means 142 controls the operation of liquid injection mechanism 117 based on the control data. For example, when a variable pattern for changing the injection rate of the contrast medium over time is recorded as data in liquid chip 214 of contrast medium syringe 200C, computer unit 130 changes the operation rate of contrast medium injection mechanism 117C over time in accordance with the variable pattern.

Data registering means 143 corresponds to the function of CPU 131 which controls the operation of patient chart reader/writer 123 in accordance with the computer program and the data entered through main operation panel 103. If the data representing inappropriateness of injection is entered on main operation panel 103, data registering means 143 causes patient chart reader/writer 123 to register the acquired product ID as the inappropriate ID in the electronic chart on patient chart chip 250.

Computer unit 130 also controls liquid injection mechanism 117 to be inoperative and provides an alarm message such as "Inappropriateness of injection is entered. Injection operation is being stopped" with display on main/sub touch panels 104 and 121 and with sound from speaker unit 105.

In chemical liquid injector 100 of the embodiment, liquid reader 122 is placed at the position where it detects liquid chip 214 of liquid syringe 200 mounted on injection execution head 110, so that operation control means 142 controls liquid injection mechanism 117 to be operative only while liquid reader 122 detects liquid chip 214.

For example, if liquid syringe 200 comes off injection execution head 110 during the operation of liquid injection mechanism 117, an alarm message such as "Syringe removal is detected. Make sure syringe is put appropriately" is provided with display on main/sub touch panels 104 and 121 and with sound from speaker unit 105, and the operation of liquid injection mechanism 117 is forcedly stopped.

Although the abovementioned various means of chemical liquid injector 100 are accomplished by pieces of hardware such as main/sub touch panels 104 and 121 as required, they are mainly implemented by CPU 131 as a piece of hardware functioning in accordance with the resources and the computer program stored on an information storage medium such as ROM 132.

Such a computer program is stored on an information storage medium such as RAM 133 as software for causing CPU 131 or the like to perform processing operations including the continuous monitoring of detection by liquid reader 122 and patient chart reader/writer 123, the comparison between the product ID detected by liquid reader 122 and the inappropriate ID detected by patient chart reader/writer 123, the control of liquid injection mechanism 117 to be inoperative and the notification of the alarm message from main/sub touch panels 104 and 121 and speaker unit 105 when the comparison shows that the product ID matches the inappropriate ID, the control of liquid injection mechanism 117 to be operative only while liquid reader 122 detects liquid chip 214, the forced stop of liquid injection mechanism 117 and the notification of the alarm message from main/sub touch panels 104 and 121 and speaker unit 105 when the detection of liquid chip 214 by liquid reader 122 is discontinued during the operation of liquid injection mechanism 117, and the registration of the acquired product ID as the inappropriate ID in the electronic chart on patient chart chip 250 by patient chart reader/writer 123, the control of liquid injection mechanism 117 to be inoperative, and the notification of the alarm message from main/sub touch panels 104 and 121 and speaker unit 105 when the inappropriateness of injection is entered through main operation panel 103.

Operation of the Embodiment

For using chemical liquid injection system 1000 of the embodiment in the abovementioned structure, chemical liquid injector 100 is placed near imaging diagnostic unit 301 of CT scanner 300, and patient chart chip 250 is prepared for use together with liquid syringe 200 and extension tube 230 as shown in FIG. 3. In chemical liquid injector 100 of the embodiment, liquid injection mechanism 117 is initially set to be inoperative in the initial state (step S1), so that liquid injection mechanism 117 is not erroneously started in response to a wrong operation.

Figure 6:
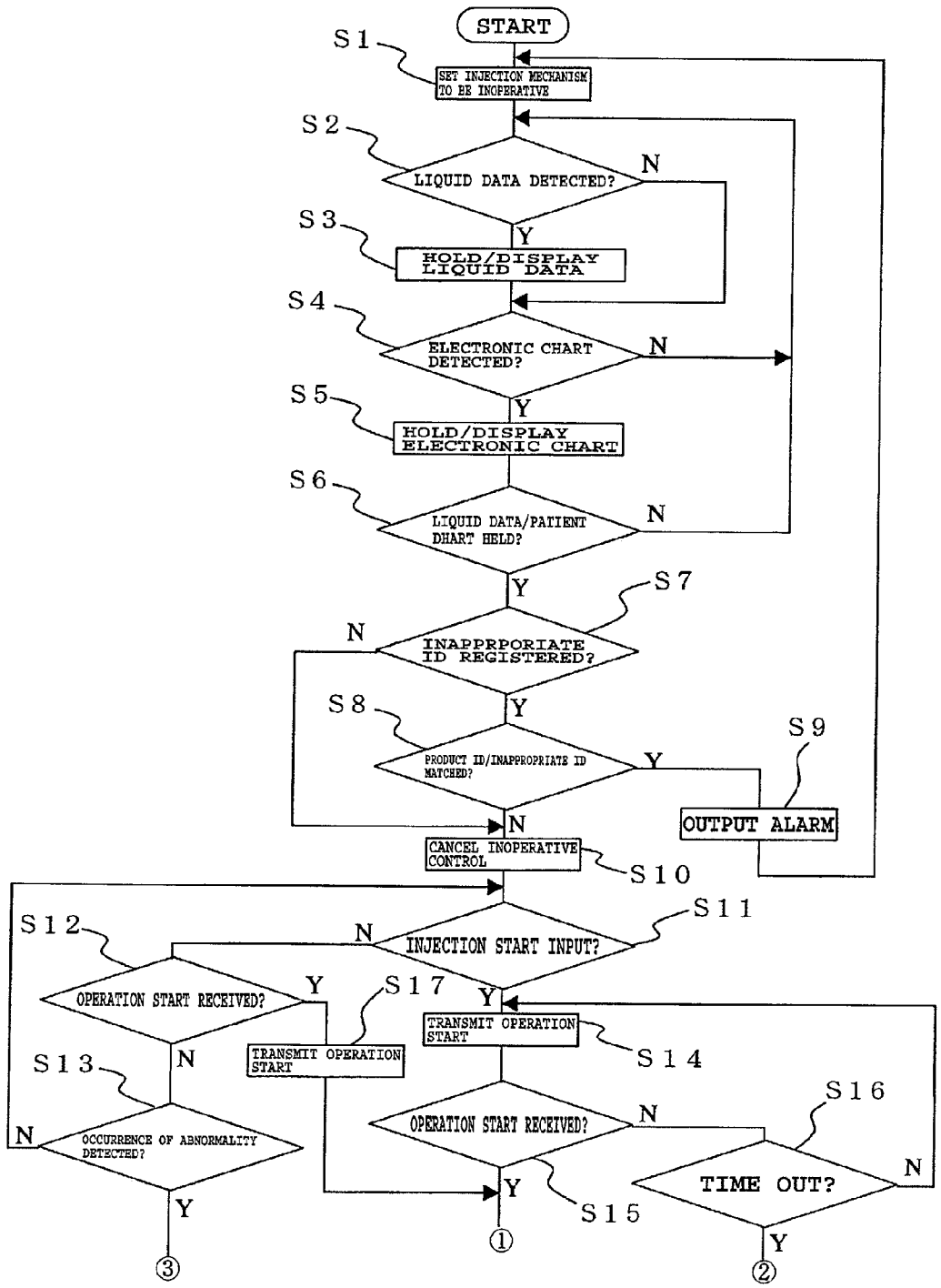
FIG. 6 is a flow chart showing the first half of the processing operation of the chemical liquid injector.

Then, liquid syringe 200 is appropriately mounted on injection execution head 110 of chemical liquid injector 100, and liquid chip 214 of liquid syringe 200 is naturally opposed to liquid reader 122 of injection execution head 110 with a predetermined distance between them. As shown in FIG. 6, the liquid data is acquired from liquid chip 214 by liquid reader 122 (step S2). The liquid data acquired in this manner is temporarily held in RAM 133 by CPU 131 of computer unit 130 and output with display on main/sub touch panels 104 and 121 (step S3), which allows an operator to see the registered liquid data.

The registered liquid data on liquid chip 214 includes various types of data to be displayed and various types of data not to be displayed. For example, a binary flag is set in each data to indicate whether or not the data should be displayed. Chemical liquid injector 100 appropriately selects some of the various types of data acquired from liquid chip 214 for display.

When the various types of data acquired from liquid chip 214 into chemical liquid injector 100 include control data such as "resistance to pressure," "capacity," and "variable pattern for changing the injection rate of the contrast medium over time," then the control data is set in computer unit 130 (step S3). When such control data is not included in the data acquired from liquid chip 214, default control data is set.

In chemical liquid injector 100 of the embodiment, when patient chart chip 250 is loaded on patient chart reader/writer 123 of injection execution head 110, the electronic chart is acquired from patient chart chip 250 by patient chart reader/writer 123 (step S4). The electronic chart acquired in this manner is also temporarily held and output with display on main/sub touch panels 104 and 121 (step S5), thereby allowing the operator to see the registered data in the electronic chart.

After both of the liquid data and the data of the electronic chart are held as described above (step S6), it is checked whether or not the electronic chart includes an inappropriate ID (step S7). If no inappropriate ID is registered in the electronic chart, any liquid is not found to be inappropriate for injection into the patient, and the control of liquid injection mechanism 117 to be inoperative in the initial setting is canceled (step S10).

On the other hand, if any inappropriate ID is registered in the electronic chart (step S7), a liquid inappropriate for injection into the patient exists due to the development of a side effect or the like. In this case, the inappropriate ID is compared with the product ID (step S8). If they do not match, the liquid in liquid syringe 200 is not the liquid inappropriate for injection into the patient, so that the control of the liquid injection mechanism 117 to be inoperative in the initial setting is canceled (step S10).

On the other hand, if the inappropriate ID matches the product ID (step S8), the liquid in liquid syringe 200 is the liquid inappropriate for injection into the patient. An alarm message such as "This liquid should not be injected into this patient" is output with display on main/sub touch panels 104 and 121 and with sound from speaker unit 105 (step S9).

In this case, the control of liquid injection mechanism 117 to be inoperative in the initial setting is not canceled and chemical liquid injector 110 returns to the initial state (step S1), which prevents the inappropriate liquid from being injected into the patient. In addition, since the alarm message can notify the operator that the liquid cannot be injected into the patient, the operator can take measures by replacing liquid syringe 200 with another type, for example.

When any inappropriate ID is not registered in the electronic chart or the inappropriate ID does not match the product ID and thus the control of liquid injection mechanism 117 to be inoperative is canceled (step S10), the operator makes entry to start operation into main/sub touch panels 104 and 121 or main operation panel 103. Then, chemical liquid injector 100 detects the entry (step S11) and transmits data for starting operation to CT scanner 300 (step S14).

Figure 8:
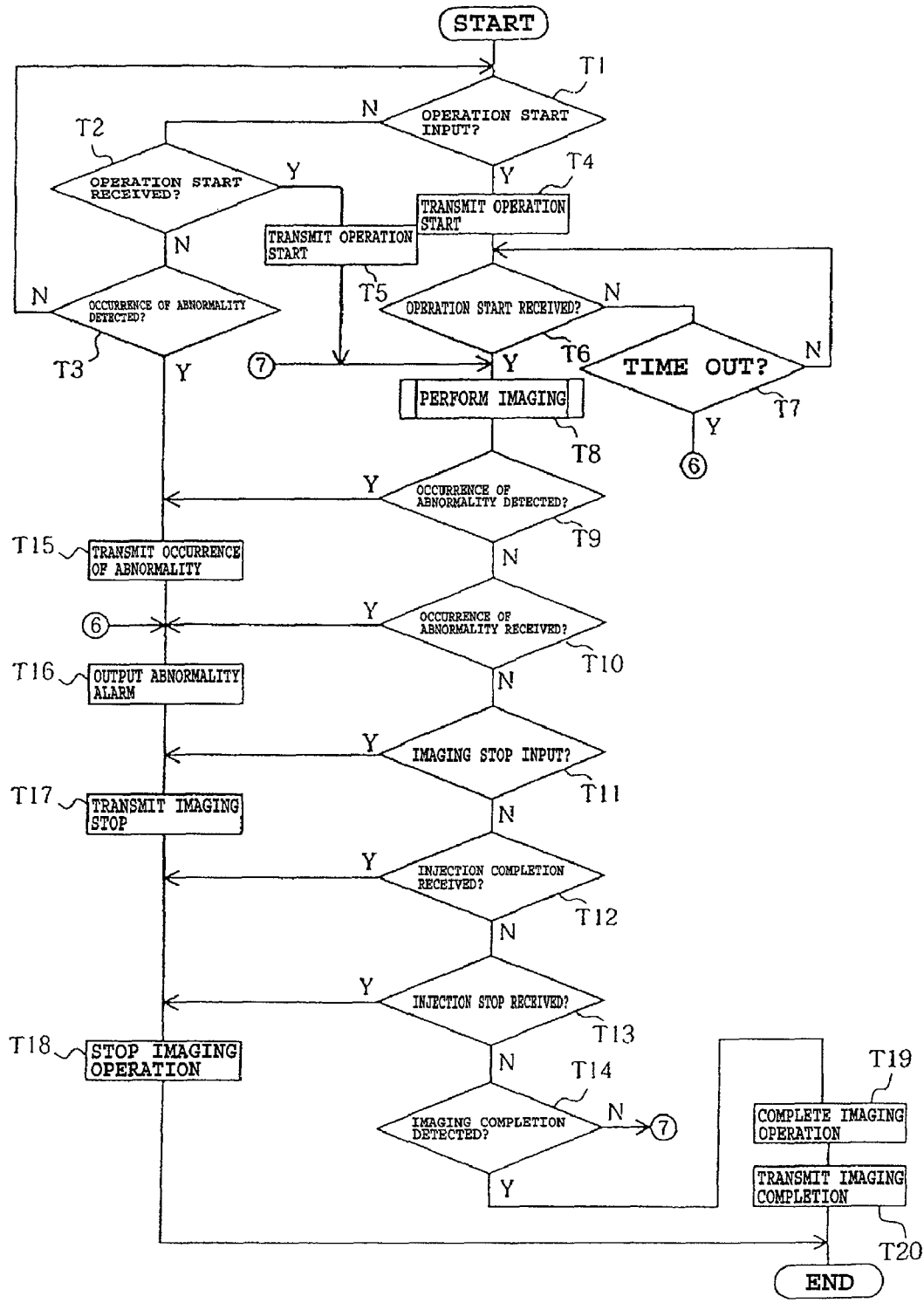
FIG. 8 is a flow chart showing the processing operation of the CT scanner.

Referring to FIG. 8, CT scanner 300 receives the data for staring operation from chemical liquid injector 100 (step T2) and transmits the data for starting operation back to chemical liquid injector 100 and performs imaging operation (step T8). Thus, in chemical liquid injection system 1000 of the embodiment, the imaging of CT scanner 300 follows the liquid injection of chemical liquid injector 100.

As shown in FIGS. 6 and 8, in chemical liquid injection system 1000 of the embodiment, when chemical liquid injector 100 is ready as described above (steps S11 to S13) and the operator makes entry to start operation to CT scanner 300 (step T1), the liquid injection of chemical liquid injector 100 follows the imaging of CT scanner 300 (steps T4, T6 and subsequent steps, steps S12, S18 and subsequent steps).

Figure 7:
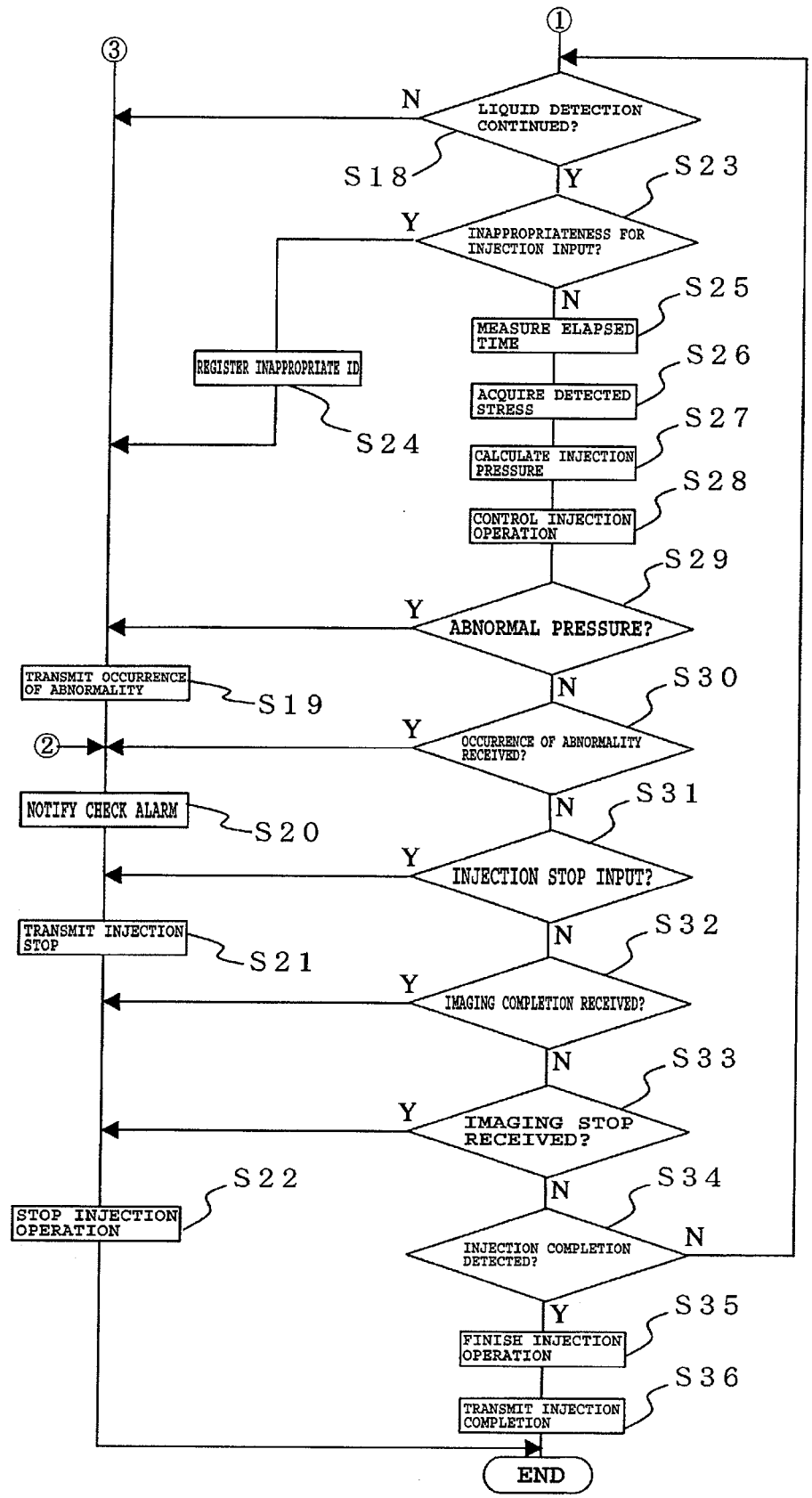
FIG. 7 is a flow chart showing the second half of the processing operation.

As shown in FIG. 7, when a series of liquid injection operations is performed (step S18 and subsequent steps) in chemical liquid injector 100 of the embodiment, the elapsed time from the start of the injection is measured (step S25), and the operations of control medium injection mechanism 117C and physiological saline injection mechanism 117W are sequentially controlled in real time based on the elapsed time and the control data acquired from liquid chip 214 (step S28).

If the variable pattern for changing the injection rate of the contrast medium over time is set in liquid chip 214 of control medium syringe 200C, the operation rate of contrast medium injection mechanism 117C is changed over time in accordance with the variable pattern. If the injection pattern for starting the injection of physiological saline following the completion of injection of the contrast medium is set in liquid chip 214 of physiological saline syringe 200W, the operation of physiological saline injection mechanism 117W is controlled in accordance with the injection pattern.

When liquid injection mechanism 117 is driven as described above, the stress detected by load cell 119 is acquired in real time by computer unit 130 (step S26). The injection pressure of the liquid is calculated from the stress detected by load cell 119 based on the viscosity of the liquid, the inner diameter of cylinder member 210 and the like acquired from liquid chip 214 (step S27). The operation of liquid injection mechanism 117 is controlled in real time such that the injection pressure falls within the pressure range acquired from liquid chip 214 (step S28).

If the resistance to pressure is set on liquid chip 214 of liquid syringe 200, the operation of liquid injection mechanism 117 is controlled in accordance with the resistance to pressure. Thus, when various types of liquid syringes 200 are mounted on chemical liquid injector 100, each liquid syringe 200 is not driven beyond the resistance to pressure, thereby reliably preventing any damage to liquid syringe 200.

While liquid syringe 200 is driven by liquid injection mechanism 117 as described above, liquid chip 214 is continuously detected by liquid reader 122 (step S18). If the abovementioned detection is discontinued (step S18) before the completion of the injection operation (step S34), the injection operation performed by liquid injection mechanism 117 is stopped (step S22).

In addition, an alarm message, for example "Syringe removal is detected. Make sure syringe is put appropriately" is output with display on main/sub touch panels 104 and 121 and with sound from speaker unit 105 (step S20). The occurrence of abnormality and the stop of injection are transmitted as data to CT scanner 300 (steps S19 and S22).

Then, CT scanner 300 receives the data representing the occurrence of abnormality (step T10) and outputs the occurrence of abnormality as a check alarm with guidance display or the like (step T16). When it receives the data representing the stop of operation (step T13), the imaging operation is stopped (step S18).

If the development of a side effect by the patient is found by the operator during the injection of the liquid into the patient from liquid syringe 200 in chemical liquid injector 100 as described above, the operator enters data representing the inappropriateness of injection through a dedicated switch or the like on main operation panel 103. Chemical liquid injector 100 detects the entry (step S23) and stops the injection operation performed by liquid injection mechanism 117 (step S22).

Then, an alarm message such as "Inappropriateness of injection is entered. Injection operation is being stopped" is output with display on main/sub touch panels 104 and 121 and with sound from speaker unit 105 (step S20). The occurrence of abnormality and the stop of injection are transmitted as data to CT scanner 300 (steps S19 and S22).

The product ID acquired from liquid syringe 200 is registered as the inappropriate ID on patient chart chip 250 (step S24). The injection of the liquid into the patient will be automatically prevented by chemical liquid injector 100 in the future (steps S8, S9).

In chemical liquid injector 100 and CT scanner 300 of the embodiment, when the occurrence of abnormality is detected in the abovementioned ready state (steps S13 and T3) or when the occurrence of abnormality is detected during the operation (steps S29 and T9), the occurrence of abnormality is notified (steps S20 and T16) and the operation is stopped (steps S22 and T18).

Since the occurrence of abnormality in one of them is transmitted to the other (steps S19 and T15), the other receives the data (steps T10 and S30) and then notifies the occurrence of abnormality (steps T16 and S20). Since the operation stop in one of them is transmitted to the other (steps S21 and T17), the other receives the data (steps T13 and S33) and stops the operation (steps T18 and S22).

When one of them receives entry to stop operation (steps S31 and T11), the one stops the operation (steps S22 and T18) and transmits it to the other (steps S21 and T17). The other receives the data (steps T13 and S33) and stops the operation (steps T18 and S22).

When the completion of the operation is detected in one of them (steps S34 and T14), the operation is ended (steps S35 and T19) and the end of the operation is transmitted to the other (steps S36 and T20). The other receives the data (steps T12 and S33) and stops the operation (steps T18 and S22).

Effect of the Embodiment

In chemical liquid injection system 1000 of the embodiment, chemical liquid injector 100 acquires the product ID from liquid chip 214 on liquid syringe 200, acquires the inappropriate ID from patient chart chip 250, and issues the alarm message if the product ID matches the inappropriate ID.

For example, when the liquid to be injected into the patient is of an appropriate type but cannot be injected into the patient for a personal reason such as the development of a side effect, that fact is automatically detected by chemical liquid injector 100 and the operator is notified of the fact. This allows the operator to quickly recognize the fact and take measures by replacing the liquid with another one, for example.

Particularly, in chemical liquid injector 100 of the embodiment, when liquid syringe 200 and patient chart chip 250 are put on injection execution head 110, the product ID and the inappropriate ID are automatically acquired and compared. This can eliminate the need of any dedicated operation for the acquirement and comparison to achieve the easy and reliable comparison of the product ID and the inappropriate ID.

The alarm message indicating that the liquid is inappropriate for injection is output with display on sub touch panel 121 of injection execution head 110 on which liquid syringe 200 and patient chart chip 250 are put. The operator who put liquid syringe 200 and patient chart chip 250 on injection execution head 110 can be quickly and reliably notified of the inappropriateness of injection.

In chemical liquid injection system 1000 of the embodiment, since at least some of the various types of data acquired from liquid chip 214 and patient chart chip 250 are held and output with display on main/sub touch panels 104 and 121, the operator can check the various types of data about the liquid and the patient easily and reliably.

In chemical liquid injection system 1000 of the embodiment, the data of the electronic chart for each patient is registered on patient chart chip 250 from which chemical liquid injector 100 acquires the inappropriate ID. This enables chemical liquid injector 100 to easily acquire the inappropriate ID for each patient without fail and eliminates the need to transmit the data of the electronic chart including the private information of the patient.

In chemical liquid injector 100 of the embodiment, liquid injection mechanism 117 is initially set to be inoperative in the initial state, and the inoperative control is not canceled unless it is ensured that any inappropriate ID is not registered on patient chart chip 250 or that the product ID does not mach the inappropriate ID. Thus, chemical liquid injection is not started by an erroneous operation, thereby reliably and automatically preventing the injection of an inappropriate liquid into the patient.

In chemical liquid injector 100 of the embodiment, when the operator makes entry representing that the liquid is inappropriate for injection during the liquid injection, the injection operation performed by liquid injection mechanism 117 is forcedly stopped. This can prevent the continued liquid injection after the patient develops a side effect, for example. When the entry representing the inappropriateness of injection is made as described above, chemical liquid injector 100 registers the product ID acquired from liquid syringe 200 as the inappropriate ID in the electronic chart on patient chart chip 250. In this manner, the inappropriate ID can be registered in the electronic chart simply and quickly in a medical facility where the liquid is actually injected into the patient, and chemical liquid injector 100 will automatically prevent injection of the liquid into the patient in the future.

In chemical liquid injector 100 of the embodiment, computer unit 130 allows liquid injection mechanism 117 to operate only while liquid reader 122 detects liquid chip 214. If liquid syringe 200 comes off the appropriate position during the liquid injection, the liquid injection can be stopped automatically.

Since the mechanism for detecting the removal of liquid syringe 200 comprises liquid chip 214 and liquid reader 122 for transferring the various types of data from liquid syringe 200 to chemical liquid injector 100, the removal of liquid syringe 200 can be detected by using the simple structure without requiring a dedicated sensor mechanism.

Sub touch panel 121 which displays the various types of data acquired from liquid/patient chart chips 214 and 250 also receives entry. When chemical liquid injector 100 performs various types of operations based on the liquid data or the like, the operator can easily control the various types of operations as required by making entry into sub touch panel 121.

In chemical liquid injection system 1000 of the embodiment, when the variable pattern for changing the injection rate of the constant medium over time is recorded on liquid chip 214 of liquid syringe 200 of the pre-filled type filled with the contrast medium, chemical liquid injector 100 changes the injection rate of the contrast medium over time in accordance with the variable pattern.

Consequently, the optimal image contrast can be maintained favorably, and the amount of the injected contrast medium can be minimized to reduce physical burdens on the patient. In addition, it is not necessary to previously register the data of the complicated variable pattern in chemical liquid injector 100. For example, a new variable pattern for a new contrast medium can be simply input to chemical liquid injector 100 from liquid chip 214 of liquid syringe 200.

In chemical liquid injector 100 of the embodiment, the pressure of the injected liquid is detected from the stress applied to piston member 220 of liquid syringe 200, and if the injection pressure reaches an abnormal level, the check alarm is output and the injection operation is forcedly stopped. This can prevent the medical malpractice of injection of the liquid at an abnormal pressure.

The determination of the pressure of the liquid by chemical liquid injector 100 as described above requires not only the stress applied to piston member 220 of liquid syringe 200 but also the various types of data such as the internal diameter of cylinder member 210 and the viscosity of the liquid. The various types of data are input to chemical liquid injector 100 from liquid chip 214. Thus, in chemical liquid injection system 1000 of the embodiment, chemical liquid injector 100 can appropriately detect the injection pressure of each liquid for each liquid syringe 200 without the operator performing the complicated operation of manual entry of the various types of data into chemical liquid injector 100.

In chemical liquid injection system 1000 of the embodiment, since the liquid injection in chemical liquid injector 100 is automatically associated with the imaging in CT scanner 300, the diagnostic images can be taken in an appropriate timing from the patient injected with the contrast medium and physiological saline in order in an appropriate timing.

Modifications of the Embodiment

The present invention is not in any way limited to the above-mentioned embodiment, but various changes and modifications may be made therein without departing from the scope of the invention. For example, in the above embodiment, chemical liquid injector 100 compares the product ID recorded as data on liquid syringe 200 with the inappropriate ID registered as data in the electronic chart to detect the liquid which is inappropriate for injection for each patient.

Alternatively, it is possible that the contained ingredients of the liquid are recorded as data on the liquid syringe, the ingredient inappropriate for injection is registered as an inappropriate ingredient in the electronic chart, and the contained ingredients are compared with the inappropriate ingredient. In this case, the data of appropriateness or inappropriateness of injection into the patient can be managed for each contained ingredient. For example, appropriateness or inappropriateness of injection of a liquid into a patient can be presumed correctly in the first injection of the liquid.

It is also possible that the liquid ID is recorded as data on the liquid syringe, the inappropriate ingredient is registered as data in the electronic chart, and the contained ingredients of a liquid are registered as data for each product ID in a liquid database external to the chemical liquid injector. In such a chemical liquid injection system, the chemical liquid injector acquires the product ID from the liquid syringe mounted thereon, searches the external liquid database for the contained ingredients of the liquid corresponding to the product ID, and compares the found contained ingredients with the inappropriate ingredient.

In this case, since a number of contained ingredients do not need to be recorded for each liquid syringe, the data record can be simplified to realize a data storing means for the liquid syringe by using a bar code of a small capacity, for example. In addition, the liquid database can be constructed in the manufacturer of the liquid syringe, so that the data of the contained ingredients of the liquid can be registered in detail and accurately. The above-mentioned liquid database may be constructed inside the chemical liquid injector.

Alternatively, it is possible that the chemical classification of the liquid is recorded as data on the liquid syringe, the chemical classification inappropriate for injection is registered as data as an inappropriate classification in the electronic chart, and the chemical classification is compared with the inappropriate classification. In this case, the data of appropriateness or inappropriateness of injection into the patient can be managed for each chemical classification. For example, appropriateness or inappropriateness of injection of a liquid into a patient can be presumed correctly in the first injection of the liquid.

It is also possible that the liquid ID is recorded as data on the liquid syringe, the inappropriate classification is registered as data in the electronic chart, and the chemical classification is registered as data for each product ID in a liquid database external to the chemical liquid injector. The liquid database as described above may be constructed inside the chemical liquid injector.

In the above embodiment, the electronic chart is registered on patient chart chip 250 provided for each patient. For example, the electronic chart may be registered as data on a file server in the medical facility such that the chemical liquid injector acquires the electronic chart online.

In the above embodiment, the data storing means for registering the liquid ID on the liquid syringe comprises the RFID chip. The data storing means may comprise a bar code or a two-dimensional code, and the electronic chart may comprise a two-dimensional code.

In the above embodiment, injection execution head 110 on which liquid syringe 200 is mounted is provided with all of liquid reader 122 for acquiring the various types of data from liquid chip 214, patient chart reader/writer 123 for acquiring the various types of data from patient chart chip 250, and sub touch panel 121 for displaying the acquired data and the alarm message, thereby providing favorable operability. The above-mentioned devices may be placed at positions away from injection execution head 110, or may be formed as portable units which are wire-connected or wirelessly connected to chemical liquid injector 100.

In the above embodiment, liquid reader 122 and patient chart reader/writer 123 are exclusively provided for liquid chip 214 and patient chart chip 250, respectively. For example, an RFID reader may be placed on the side of the injection execution head and be manually opposed to liquid chip 214 and patient chart chip 250 in order. In this case, the chemical liquid injector can acquire the product ID and the inappropriate ID with the single RFID reader to simplify the structure of the chemical liquid injector.

In the above embodiment, injection execution head 110 and injection control unit 101 of chemical liquid injector 100 are formed as the separate components and wire-connected to each other. For example, they may be wirelessly connected to each other with radio waves, ultrasonic waves, infrared rays or the like, or may be formed integrally into one unit.

To simplify the description, the above embodiment shows that liquid syringe 200 having liquid chip 214 placed thereon is directly put in chemical liquid injector 100 on which liquid reader 122 is mounted. In currently available chemical liquid injectors 100, however, only liquid syringe 200 of the largest size is directly mounted, and each of liquid syringes 200 of the sizes other than the largest size is mounted via a dedicated cylinder adapter.

Liquid reader 122 may be placed on the cylinder adapter. When the cylinder adapter is mounted on injection execution head 110, liquid reader 122 thereon may be connected to chemical liquid injector 100. Liquid chip 214 may also be placed on the cylinder adapter, and when liquid syringe 200 is mounted on injection execution head 110 with the cylinder adapter, liquid reader 122 thereon may detect liquid chips 214 of liquid syringe 200 and the cylinder adapter.

In the above embodiment, if chemical liquid injector 100 detects the removal of liquid syringe 200 during the injection operation, it forcedly stops the injection operation and notifies the occurrence of abnormality. For example, when chemical liquid injector 100 detects the removal of liquid syringe 200 after the completion of the injection operation, it may automatically return liquid injection mechanism 117 back to the initial position at the rear.

When chemical liquid injector 100 moves liquid injection mechanism 117 to the home position after the completion of the various operations and then detects mounting of new liquid syringe 200 by liquid reader 122, it may automatically move associated liquid injection mechanism 117 forward to the standby position where piston member 210 is held.

In this case, liquid syringe 200 is mounted on and removed from chemical liquid injector 100 in an appropriate timing, which automatically places liquid injection mechanism 117 to the appropriate position. Thus, any special operation is not necessary for the placement, and enhanced convenience can be achieved.

In the above embodiment, liquid chip 214 is placed on the outer circumference of cylinder member 210 of liquid syringe 200. For example, liquid chip 214 may be placed on the outer circumference or trailing end face of piston member 220.

In the embodiment, the data such as the product ID is registered by the manufacturer on liquid chip 214 of liquid syringe 200 of the pre-filled type. For example, an operator in a medical facility may register data such as a desirable product ID on liquid chip 214 of liquid syringe 200 of the refill type.

In the above embodiment, chemical liquid injector 100 having two liquid injection mechanisms 117 injects the contrast medium and physiological saline. It is also possible to realize a chemical liquid injector which injects only a contrast medium with one liquid injection mechanism 117 or a chemical liquid injector which injects three or more liquids with three or more liquid injection mechanisms 117.

In the above embodiment, CT scanner 300 is used as the imaging diagnostic apparatus and chemical liquid injector 100 injects the contrast medium for CT. For example, an MRI apparatus or a PET apparatus may be used as the imaging diagnostic apparatus and the chemical liquid injector may inject a contrast medium therefore.

In the above embodiment, CPU 131 operates in accordance with the computer program stored in RAM 133 or the like to realize logically various means as various functions of chemical liquid injector 100. Each of the various means may be formed as specific hardware, or some of them may be stored as software on RAM 133 or the like, while others may be formed as hardware.

The invention claimed is:

1. A chemical liquid injection system at least comprising:
   a liquid syringe including a cylinder member filled with a liquid and a piston member slidably inserted into the cylinder member; and
   a chemical liquid injector for injecting the liquid into a patient by relatively moving the cylinder member and the piston member of the liquid syringe replaceably mounted thereon, using a liquid injection mechanism,
   wherein the liquid syringe has data storing means on which liquid-identification data for the filled liquid and an injection pattern for varying the injection rate with time are recorded, and the chemical injector further comprises operation control means configured to control the liquid injection mechanism by changing the operation rate of the liquid injection mechanism with time in accordance with the injection pattern,
   wherein the chemical liquid injector includes:
   liquid data acquiring means for acquiring the data from the data storing means;
   patient chart data acquiring means for acquiring data on contra-indicated liquid from an external electronic chart, wherein at least identification data for the contra-indicated liquid for injection are registered as the data on contra-indicated liquid in the electronic chart for each of the patients;
   data comparing means for comparing the acquired liquid-identification data and the acquired data on contra-indicated liquid; and
   alarm notifying means for notifying an alarm when the liquid-identification data matches the data on contra-indicated liquid.

2. The chemical liquid injection system according to claim 1, wherein the liquid-identification data and the data on contra-indicated liquid include data of a product ID, and the chemical liquid injector further comprise:
   input operation means for receiving an input operation indicating inappropriateness of injection during the operation of the liquid injection mechanism; and
   data registering means for registering the acquired product ID as inappropriateness ID in the electronic chart when the input operation indicating inappropriateness of injection is performed.

3. The chemical liquid injection system according to claim 1, wherein the operation control means is further configured to control the liquid injection mechanism to be inoperative when the data comparing means detects the matching.

4. The chemical liquid injection system according to claim 3, wherein the chemical liquid injector includes an injection control unit on which at least the operation control means is mounted, and an injection execution head formed as a separate component from the injection control unit, at least the liquid injection mechanism, the liquid data acquiring means, and the alarm notifying means being mounted on the injection execution head.

5. The chemical liquid injection system according to claim 3, wherein the liquid data acquiring means is placed at a position to detect the data storing means of the liquid syringe mounted on the chemical liquid injector, and
   the operation control means controls the liquid injection mechanism to be operative only while the liquid data acquiring means detects the data storing means.

6. The chemical liquid injection system according to claim 5, wherein the operation control means returns the liquid injection mechanism to an initial position after the completion of an injection operation is detected and then the detection of the data storing means by the liquid data acquiring means is ended.

7. The chemical liquid injection system according to claim 3, wherein the data storing means which comprises an RFID (Radio Frequency Identification) chip is put on the liquid syringe, and
   the chemical liquid injector includes the liquid data acquiring means which comprises an RFID reader.

8. The chemical liquid injection system according to claim 7, wherein the electronic chart which comprises an RFID chip is provided for each of the patients, and
   the patient chart data acquiring means of the chemical liquid injector acquires data from the electronic chart with the liquid data acquiring means.

9. The chemical liquid injection system according to claim 1, wherein the electronic chart which comprises an RFID chip is provided for each of the patients, and
   the chemical liquid injector includes the patient chart data acquiring means which comprises an RFID reader.

10. The chemical liquid injection system according to claim 1, wherein the liquid-identification data and the data on contra-indicated liquid each include at least data selected from the group consisting of a product ID, a contained ingredient, and a chemical classification.

11. The chemical liquid injection system according to claim 1, wherein
    the liquid-identification data recorded on the data storing means includes data of a product ID,
    at least data of a contained ingredient of the contra-indicated liquid for injection being registered as the data on contra-indicated liquid in the electric chart,
    the chemical liquid injector further comprises data retrieving means for retrieving a contained ingredient as the liquid-identification data from an external liquid database with the acquired product ID, at least the contained ingredient being registered in the liquid database for each of the product IDs, and
    the comparing means compares the liquid-identification data acquired by retrieving with the data retrieving means and the data on contra-indicated liquid acquired from the patient chart data acquiring means.

12. The chemical liquid injection system according to claim 1, wherein
    the liquid-identification data recorded on the data storing means includes data of a product ID,
    at least data of a contained ingredient of the contra-indicated liquid for injection being registered as the data on contra-indicated liquid in the electric chart,
    the chemical liquid injector further comprises ingredient storing means in which at least data of a contained ingredient for each of the product IDs is registered, and data retrieving means for retrieving the contained ingredient as the liquid-identification data from the ingredient storing means with the acquired product ID, and the comparing means compares the liquid-identification data acquired by retrieving with the data retrieving means and the data on contra-indicated liquid acquired from the patient chart data acquiring means.

13. The chemical liquid injection system according to claim 1, wherein the liquid-identification data recorded on the data storing means includes data of a product ID, at least data of a chemical classification of the contra-indicated liquid for injection being registered as the data on contra-indicated liquid in the electric chart, the chemical liquid injector further comprises data retrieving means for retrieving a chemical classification as the liquid-identification data from an external liquid database with the acquired product ID, at least the chemical classification being registered in the liquid-identification database for each of the product IDs, and the comparing means compares the liquid-identification data acquired by retrieving with the data retrieving means and the data on contra-indicated liquid acquired from the patient chart data acquiring means.

14. The chemical liquid injection system according to claim 1, wherein the liquid-identification data recorded on the data storing means includes data of a product ID, at least data of a chemical classification of the contra-indicated liquid for injection being registered as the data on contra-indicated liquid in the electric chart, the chemical liquid injector further comprises classification storing means in which at least data of a chemical classification for each of the product IDs is registered, and data retrieving means for retrieving the chemical classification as the liquid-identification data from the ingredient storing means with the acquired product ID, and the comparing means compares the liquid-identification data acquired by retrieving with the data retrieving means and the data on contra-indicated liquid acquired from the patient chart data acquiring means.

15. A chemical liquid injector for injecting liquid into a patient by moving relatively a cylinder member and a piston member of a liquid syringe mounted replaceably on the chemical liquid injector, said liquid syringe having data storing means on which liquid identification data of the filled liquid and an injection pattern for varying the injection rate with time are recorded, said chemical liquid injector comprising:

operation control means configured to control a liquid injection mechanism by changing the operation rate of the liquid injection mechanism with time in accordance with the injection pattern;

liquid data acquiring means for acquiring the data from the data storing means;

patient chart data acquiring means for acquiring date on contra-indicated liquid from an external electronic chart, wherein at least identification data for the contra-indicated liquid for injection are registered as the data on contra-indicated liquid in the electronic chart for each of the patients;

data comparing means for comparing the acquired liquid-identification data and the data on contra-indicated liquid; and alarm notifying means for notifying an alarm when the liquid-identification data matches the data on contra-indicated liquid.

16. A chemical liquid injection system comprising:

(a) a liquid syringe comprising a cylinder member to be filled with a liquid and a piston member slidably inserted into the cylinder member, said liquid syringe further comprises data storing means being configured to store liquid-identification date for the liquid and an injection pattern for varying the injection rate of the liquid with time; and (b) a chemical liquid injector for injecting the liquid into a patient by relatively moving the cylinder member and the piston member of the liquid syringe mounted thereon, said chemical liquid injector comprising:

operation control means configured to control a liquid injection mechanism by changing the operation rate of the liquid injection mechanism with time in accordance with the injection pattern;

a liquid-identification data reader for acquiring the date from the liquid syringe;

a patient data reader for acquiring data on contra-indicated liquid from an external electronic chart for the patent;

a data comparing unit for comparing the liquid-identification date and the date on contra-indicated liquid; and a notifying device for notifying an outcome from the date comparing unit when the liquid-identification date are matched to the date on contra-indicated liquid.

17. A method of injecting a chemical liquid into a patient comprising:

providing a data carrier mounted on a liquid syringe, said data carrier having liquid-identification data for the filled liquid and an injection pattern for varying the injection rate with time recorded thereon, replaceably mounting the liquid syringe on a chemical liquid injector, said liquid syringe comprising a cylinder member filled with a liquid and a piston member slidably inserted into the cylinder member;

acquiring liquid-identification data from the data carrier;

acquiring data on contra-indicated liquid from an external electronic chart, wherein at least identification data for the contra-indicated liquid for injection are registered as the data on contra-indicated liquid in an electronic chart for each of the patients;

comparing the acquired liquid-identification data and the acquired data on contra-indicated liquid;

notifying an alarm when the liquid-identification data matches the data on contra-indicated liquid;

injecting the liquid into a patient by relatively moving the cylinder member and the piston member of the liquid syringe; and controlling the injection by changing the operation rate of the liquid injection mechanism with time in accordance with the injection pattern.

* * * * *

UNITED STATES PATENT AND TRADEMARK OFFICE
CERTIFICATE OF CORRECTION

PATENT NO. : 7,828,776 B2  
APPLICATION NO. : 11/911139  
DATED : November 9, 2010  
INVENTOR(S) : Shigeru Nemoto et al.

Page 1 of 1

It is certified that error appears in the above-identified patent and that said Letters Patent is hereby corrected as shown below:

On Sheet 6 of 8, Box S7, Figure 6, Line 1, change "INAPPRPORIATE" to --INAPPROPRIATE--.

In Column 2, Line 47-48 (Approx.), change "above-mentioned" to --abovementioned--.

In Column 5, Line 56, change "Injection Execution Head" to --INJECTION EXECUTION HEAD--.

In Column 5, Line 63, change "Operation Control Means" to --OPERATION CONTROL MEANS--.

In Column 7, Line 30, change "001" to --101--.

In Column 13, Line 45 (Approx), change "mach" to --match--.

In Column 14, Line 61, change "above-mentioned" to --abovementioned--.

In Column 15, Line 29, change "above-mentioned" to --abovementioned--.

In Column 19, Line 59, in Claim 15, change "date" to --data--.

In Column 20, Line 15, in Claim 16, change "date" to --data--.

In Column 20, Line 26, in Claim 16, change "the date" to --the data--.

In Column 20, Line 31, in Claim 16, change "date and" to --data and--.

In Column 20, Line 32, in Claim 16, change "the date" to --the data--.

In Column 20, Line 33, in Claim 16, change "date are" to --data are--.

In Column 20, Line 34, in Claim 16, change "date on" to --data on--.

Signed and Sealed this  
Thirty-first Day of January, 2012

David J. Kappos  
*Director of the United States Patent and Trademark Office*